US009833222B2

(12) United States Patent
Fiebig

(10) Patent No.: US 9,833,222 B2
(45) Date of Patent: *Dec. 5, 2017

(54) BIOPSY DEVICE WITH MOTORIZED NEEDLE FIRING

(71) Applicant: Devicor Medical Products, Inc., Cincinnati, OH (US)

(72) Inventor: Kevin M. Fiebig, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 573 days.

This patent is subject to a terminal disclaimer.

(21) Appl. No.: 14/463,910

(22) Filed: Aug. 20, 2014

(65) Prior Publication Data

US 2014/0358031 A1 Dec. 4, 2014

Related U.S. Application Data

(63) Continuation of application No. 13/086,567, filed on Apr. 14, 2011.

(51) Int. Cl.
*A61B 10/02* (2006.01)
*A61B 17/00* (2006.01)
*A61B 90/00* (2016.01)

(52) U.S. Cl.
CPC ...... *A61B 10/0275* (2013.01); *A61B 10/0283* (2013.01); *A61B 2010/0208* (2013.01);
(Continued)

(58) Field of Classification Search
CPC ........ A61B 10/0275; A61B 2090/0808; A61B 10/0283; A61B 2017/0046; A61B 2017/00561; A61B 2010/0208
See application file for complete search history.

(56) References Cited

U.S. PATENT DOCUMENTS 5,492,130 A * 2/1996 Chiou ................ A61B 10/0283
600/566
5,526,822 A 6/1996 Burbank et al.
(Continued)

FOREIGN PATENT DOCUMENTS

AU 2012243067 B2 5/2014
CN 101548898 A 10/2009
(Continued)

OTHER PUBLICATIONS

Japanese Office Action dated Mar. 16, 2016 for Application No. JP 2014-505207, 2 pgs.
(Continued)

*Primary Examiner* — Rene Towa
(74) *Attorney, Agent, or Firm* — Frost Brown Todd LLC

(57) ABSTRACT

A biopsy device comprises a needle, a body portion, and a needle firing assembly. The needle firing assembly is operable to fire the needle distally relative to the body portion. The needle firing assembly includes two translating members, a resilient member, and a motor. The motor is operable to selectively move the first translating member distally and proximally. The second translating member is secured relative to the needle such that the needle and the second translating member translate unitarily. The resilient member compresses as the first translating member is moved distally toward the second translating member. The first translating member is then secured to the second translating and the translating members are moved proximally while holding the resilient member in the compressed state. The second translating member is released from the first translating member when they reach a proximal position, which allows the resilient member to fire the needle distally.

20 Claims, 14 Drawing Sheets

(52) U.S. Cl.
CPC .......... *A61B 2017/0046* (2013.01); *A61B 2017/00561* (2013.01); *A61B 2090/0808* (2016.02)

(56) References Cited

U.S. PATENT DOCUMENTS

| | | | |
|---|---|---|---|
| 6,592,530 B1* | 7/2003 | Farhadi | A61B 10/0275 600/564 |
| 6,626,849 B2 | 9/2003 | Huitema et al. | |
| 6,806,544 B2 | 10/2004 | Liu | |
| 7,147,607 B2 | 12/2006 | Wang | |
| 7,442,171 B2 | 10/2008 | Stephens et al. | |
| 7,470,237 B2 | 12/2008 | Beckman et al. | |
| 7,854,706 B2 | 12/2010 | Hibner | |
| 7,867,173 B2 | 1/2011 | Hibner et al. | |
| 7,918,804 B2 | 4/2011 | Monson et al. | |
| 8,109,885 B2 | 2/2012 | Heske et al. | |
| 8,118,755 B2 | 2/2012 | Hibner et al. | |
| 8,172,773 B2 | 5/2012 | Heske et al. | |
| 8,206,316 B2 | 6/2012 | Hibner et al. | |
| 8,366,636 B2 | 2/2013 | Videbaek | |
| 8,376,957 B2 | 2/2013 | Hibner et al. | |
| 8,480,595 B2 | 7/2013 | Speeg et al. | |
| 8,672,860 B2 | 3/2014 | Moore et al. | |
| 8,702,623 B2 | 4/2014 | Parihar et al. | |
| 8,764,680 B2 | 7/2014 | Rhad et al. | |
| 8,858,465 B2 | 10/2014 | Fiebig | |
| 2002/0045840 A1* | 4/2002 | Voegele | A61B 10/0275 600/564 |
| 2006/0074345 A1 | 4/2006 | Hibner | |
| 2006/0184063 A1 | 8/2006 | Miller | |
| 2008/0195066 A1* | 8/2008 | Speeg | A61B 10/0275 604/326 |
| 2008/0214955 A1 | 9/2008 | Speeg et al. | |
| 2009/0326413 A1 | 12/2009 | Hancock | |
| 2010/0152610 A1 | 6/2010 | Parihar et al. | |
| 2010/0160819 A1 | 6/2010 | Parihar et al. | |
| 2011/0004121 A1 | 1/2011 | Drubetsky et al. | |
| 2012/0059247 A1 | 3/2012 | Speeg et al. | |

FOREIGN PATENT DOCUMENTS

| | | |
|---|---|---|
| CN | 103491881 A | 1/2014 |
| JP | 2009-125589 A | 6/2009 |
| JP | 2011-062244 A | 3/2011 |
| WO | WO 2012/142013 | 10/2012 |

OTHER PUBLICATIONS

Japanese Office Action dated Nov. 1, 2016 for Application No. JP 2014-505207, 2 pgs.
Australian Patent Examination Report No. 1, dated Nov. 28, 2013 for Application No. 2012243067.
Chinese Office Action dated Dec. 23, 2014 for Application No. CN 201280017934.5.
Chinese Office Action dated Jul. 15, 2015 for Application No. CN 201280017934.5.
European Communication dated Sep. 15, 2015 for Application No. EP 12770828.7.
Suuplementary European Search Report dated Nov. 3, 2014 for Application No. EP 12770828.7.
International Search Report and Written Opinion dated Aug. 10, 2012 for Application No. PCT/US2012/032853.
U.S. Appl. No. 61/381,466, filed Sep. 10, 2010.
Korean Office Action dated Aug. 4, 2017 for Application No. KR 2013-7029812, 4 pgs.

* cited by examiner

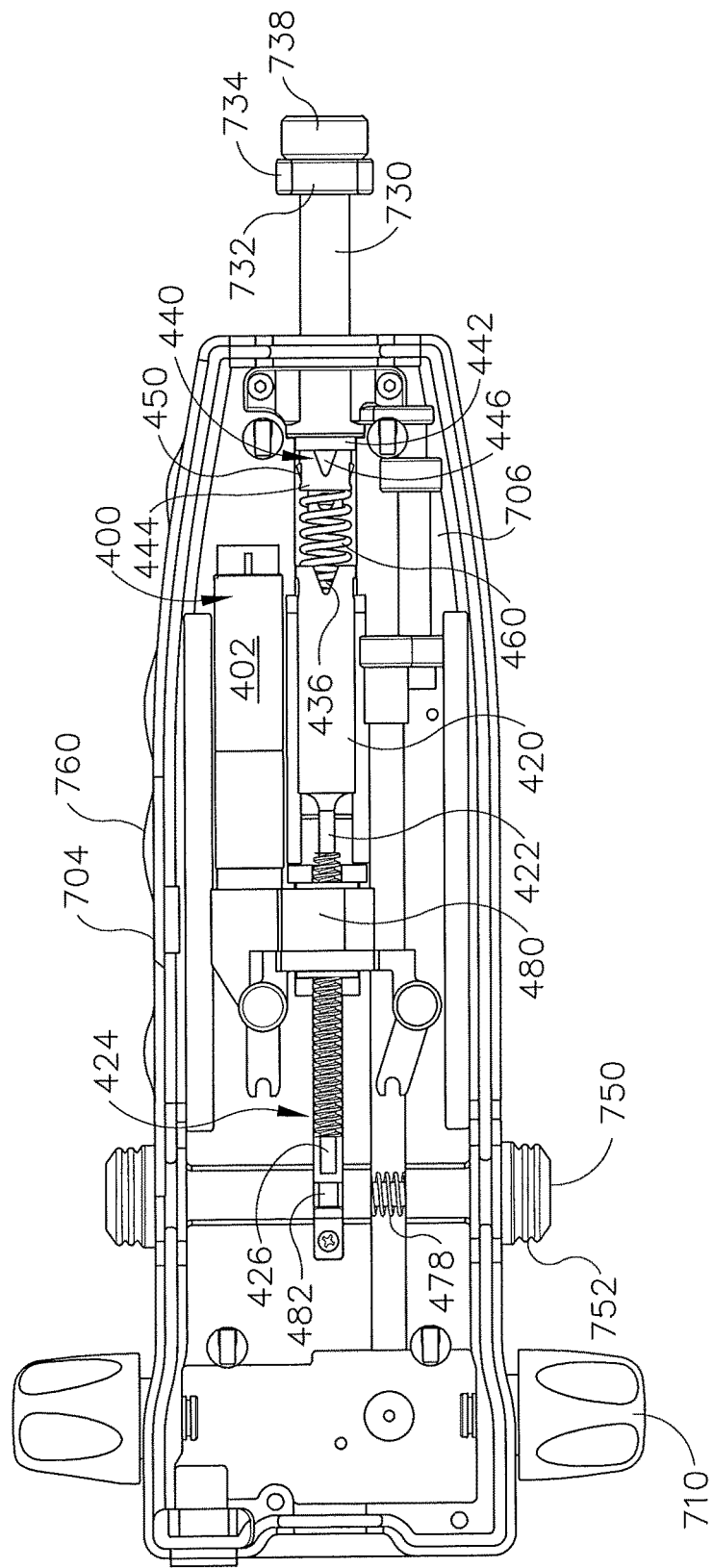

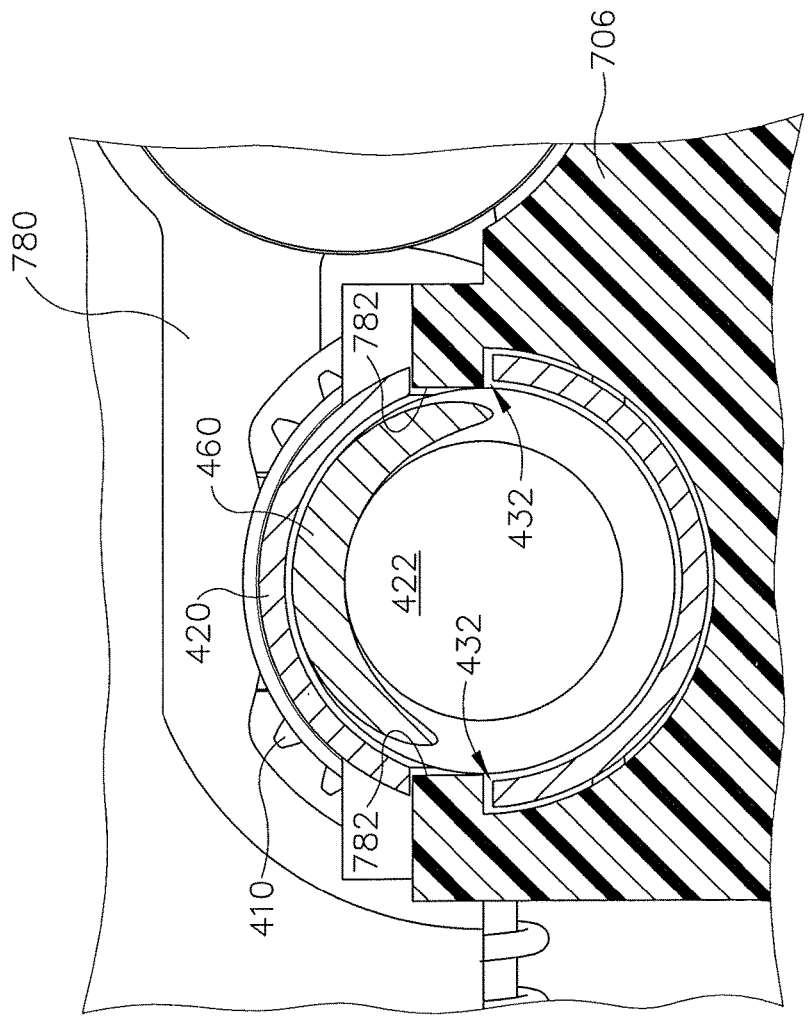

BIOPSY DEVICE WITH MOTORIZED NEEDLE FIRING

This application is a continuation of U.S. patent application Ser. No. 13/086,567, published as U.S. Patent Application Pub. No. 2012/0265095, entitled "Biopsy Device With Motorized Needle Firing," filed Apr. 14, 2011, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; and U.S. Non-Provisional patent application Ser. No. 12/953,715, entitled "Handheld Biopsy Device with Needle Firing," filed Nov. 24, 2010. The disclosure of each of the above-cited U.S. Patents, U.S. Patent Application Publications, and U.S. Non-Provisional Patent Applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 5 depicts a top plan view of the holster of the biopsy device of FIG. 2, with the top housing cover removed;

FIG. 8 depicts a cross-sectional end view of cam rails of the holster of FIG. 5 engaged with the firing tube of FIG. 7;

Figure 1:
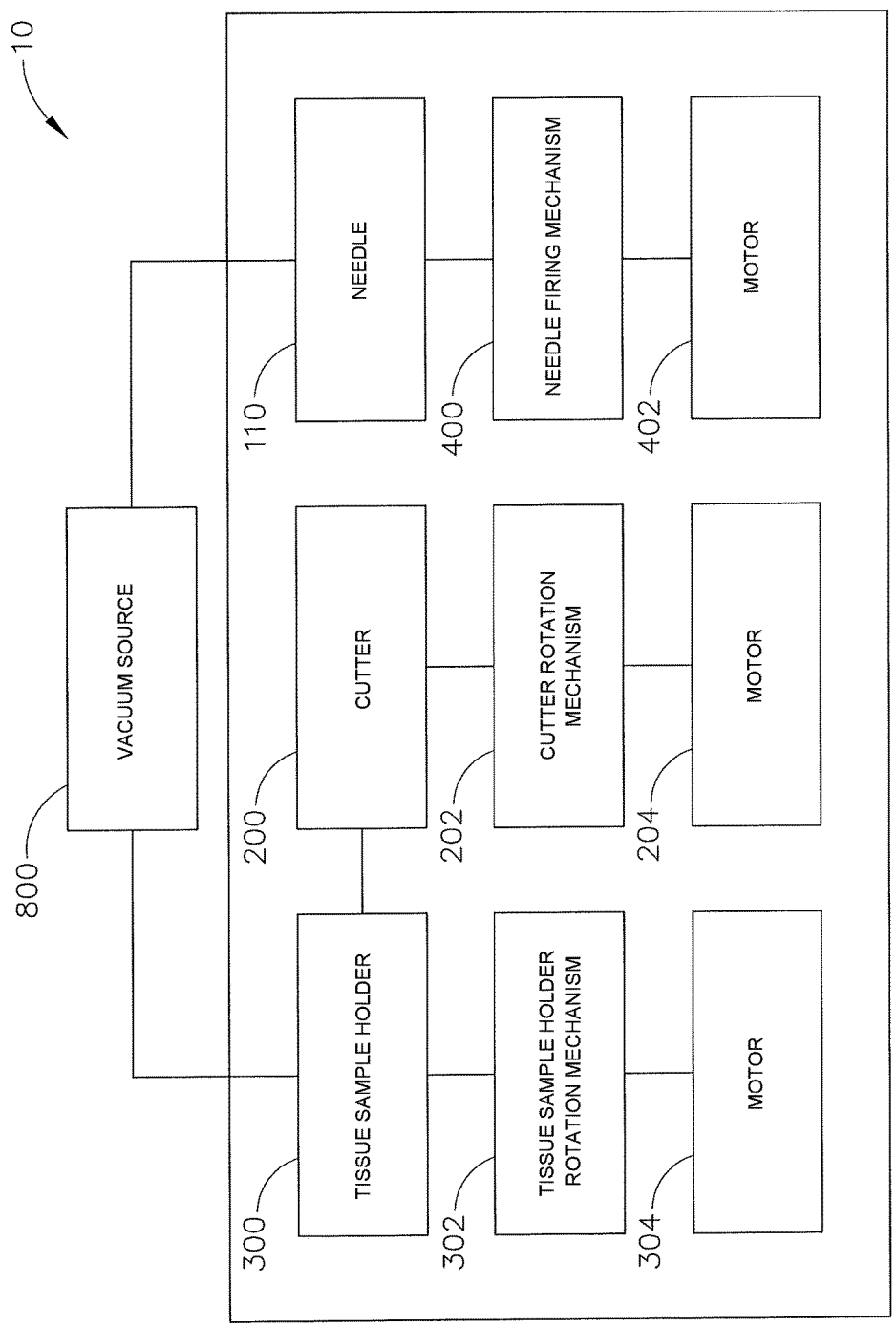
FIG. 1 depicts a block schematic diagram showing various components of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

FIGS. 1-4 show an exemplary biopsy device (10). Biopsy device (10) of this example comprises a probe (100) and a holster (700). A needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (700). While prongs (102) are used to removably secure probe (100) to holster (700) in the present example, it should be understood that a variety of other types of structures, components, features, etc. (e.g., bayonet mounts, latches, clamps, clips, snap fittings, etc.) may be used to provide removable coupling of probe (100) and holster (700). Furthermore, in some biopsy devices (10), probe (100) and holster (700) may be of unitary or integral construction, such that the two components cannot be separated. By way of example only, in versions where probe (100) and holster (700) are provided as separable components, probe (100) may be provided as a disposable component, while holster (700) may be provided as a reusable component. Still other suitable structural and functional relationships between probe (100) and holster (700) will be apparent to those of ordinary skill in the art in view of the teachings herein.

Some variations of biopsy device (10) may include one or more sensors (not shown), in probe (100) and/or in holster (700), that is/are configured to detect when probe (100) is coupled with holster (700). Such sensors or other features may further be configured to permit only certain types of probes (100) and holsters (700) to be coupled together. In addition or in the alternative, such sensors may be configured to disable one or more functions of probes (100) and/or holsters (700) until a suitable probe (100) and holster (700) are coupled together. Of course, such sensors and features may be varied or omitted as desired.

In some versions as shown in FIG. 1, biopsy device (10) includes a vacuum source (800), such as a vacuum pump. By way of example only, vacuum source (800) may be incorporated into probe (100), incorporated into holster (700), and/or be a separate component altogether. In versions where vacuum source (800) is separate from probe (100) and holster (700), vacuum source (800) may be coupled with probe (100) and/or holster (700) via one or more conduits such as flexible tubing. As shown in FIG. 1, vacuum source (800) is in fluid communication with tissue sample holder (300) and needle (110). Thus, vacuum source (800) may be activated to draw tissue into lateral aperture (114) of needle (110). Tissue sample holder (300) is also in fluid communication with cutter (200). Vacuum source (800) may thus also be activated to draw severed tissue samples through the hollow interior of cutter (200) and into tissue sample holder (300). Other suitable ways in which vacuum source (800) may be used will be apparent to those of ordinary skill in the art in view of the teachings herein. It should also be understood that vacuum source (800) may simply be omitted, if desired.

In some versions, vacuum source (800) is provided in accordance with the teachings of U.S. Pub. No. 2008/0214955, the disclosure of which is incorporated by reference herein. In addition or in the alternative, vacuum source (800) may be provided in accordance with the teachings of U.S. Non-Provisional patent application Ser. No. 12/953,715, the disclosure of which is incorporated by reference herein. As yet another merely illustrative example, vacuum source (800) may be provided in accordance with the teachings of U.S. Non-Provisional patent application Ser. No. 12/709,695, entitled "Biopsy Device with Auxiliary Vacuum Source," filed Feb. 22, 2010, the disclosure of which is incorporated by reference herein. Still other suitable ways in which vacuum source (800) may be provided will be apparent to those of ordinary skill in the art in view of the teachings herein.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Probe

Figure 2:
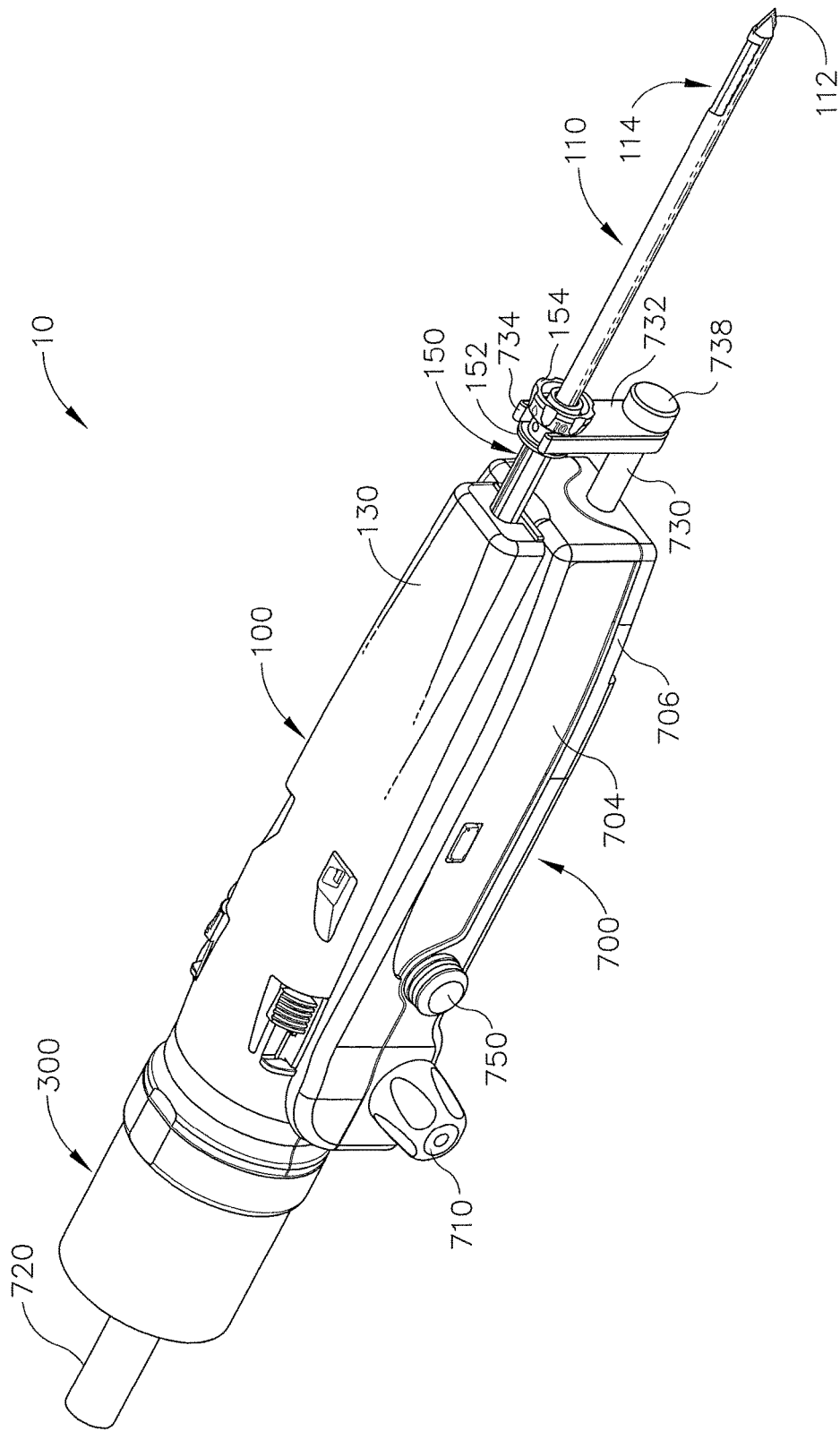
FIG. 2 depicts a perspective view of the probe and holster of an exemplary biopsy device coupled together.
Figure 3:
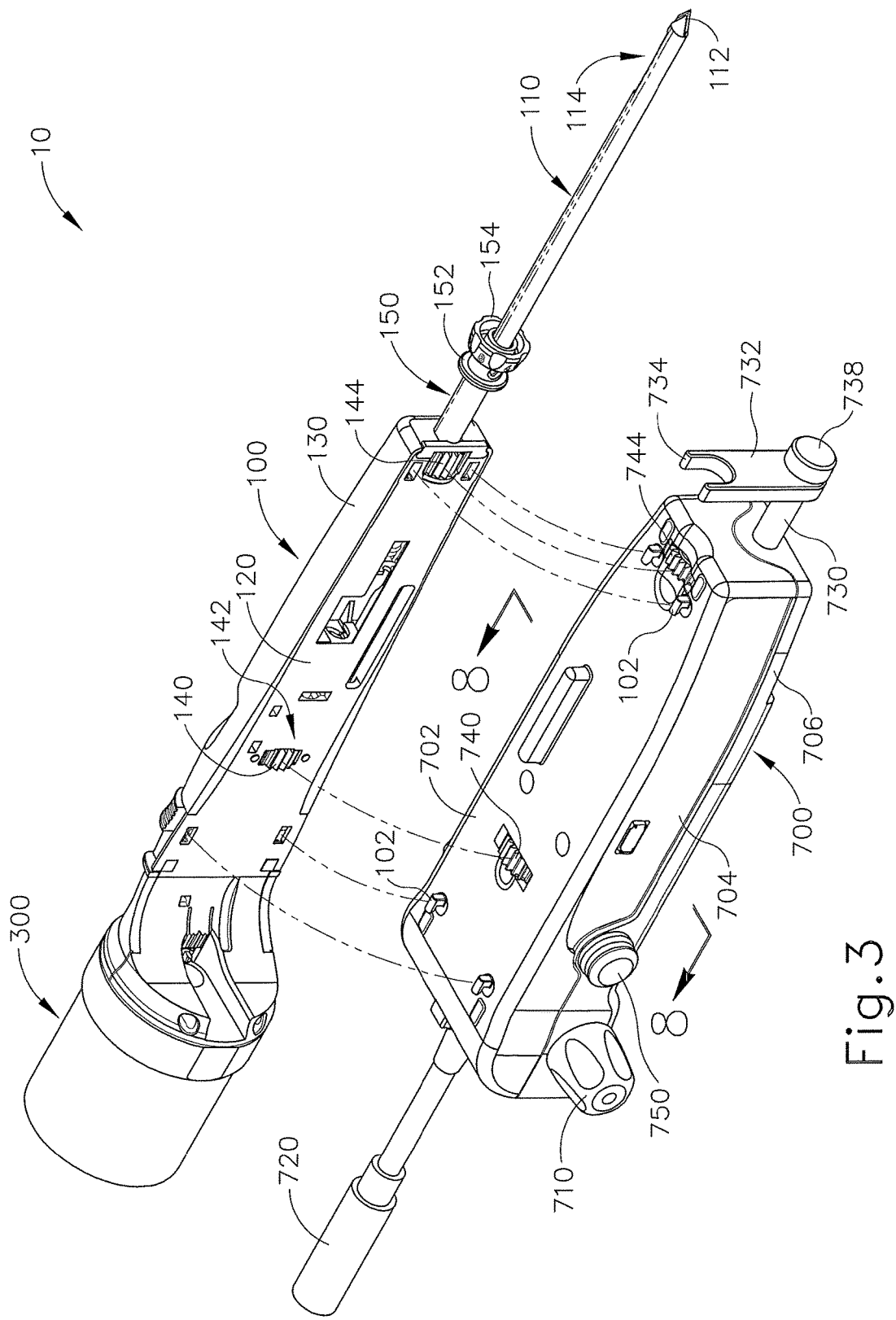
FIG. 3 depicts a perspective view of the biopsy device of FIG. 2, with the probe separated from the holster to expose an underside of the probe and a top side of the holster.

As shown in FIGS. 2-4, probe (100) of the present example includes a distally extending needle (110). Probe (100) also includes a chassis (120) and a top housing (130), which are fixedly secured together. As best seen in FIG. 3, a gear (140) is exposed through an opening (142) in chassis (120), and is operable to drive cutter actuation mechanism (202) in probe (100). As also seen in FIG. 3, another gear (144) is exposed through another opening (146) in chassis (120), and is operable to rotate needle (110) as will be described in greater detail below. Gear (140) of probe (100) meshes with exposed gear (740) of holster (700) when probe (100) and holster (700) are coupled together. Similarly, gear (144) of probe (100) meshes with exposed gear (744) of holster (700) when probe (100) and holster (700) are coupled together.

A. Exemplary Needle

Needle (110) of the present example includes a piercing tip (112), a lateral aperture (114) located proximal to tip (112), and a hub member (150). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. Tip (112) may also be configured to provide greater echogenicity than other portions of needle (110), providing enhanced visibility of tip (112) under ultrasound imaging. By way of example only, tip (112) may be configured in accordance with any of the teachings in U.S. Non-Provisional patent application Ser. No. 12/875,200, entitled "Echogenic Needle for Biopsy Device," filed Sep. 3, 2010, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (200) having a sharp distal edge (not shown) is located within needle (110). Cutter (200) is operable to rotate and translate relative to needle (110) and past lateral aperture (114) to sever a tissue sample from tissue protruding through lateral aperture (114). For instance, cutter (200) may be moved from an extended position to a retracted position, thereby "opening" lateral aperture (114) to allow tissue to protrude therethrough; then from the retracted position back to the extended position to sever the protruding tissue. While lateral aperture (114) is shown oriented in an upward position in FIG. 1, it should be understood that needle (110) may be rotated to orient lateral aperture (114) at any desired angular position about the longitudinal axis of needle (110). Such rotation of needle (110) is facilitated in the present example by hub member (150).

Hub member (150) of the present example is overmolded about needle (110), such that hub member (150) and needle (110) rotate and translate unitarily with each other. By way of example only, needle (110) may be formed of metal, and hub member (150) may be formed of a plastic material that is overmolded about needle (110) to unitarily secure and form hub member (150) to needle (110). Hub member (150) and needle (110) may alternatively be formed of any other suitable material(s), and may be secured together in any other suitable fashion. Hub member (150) includes an annular flange (152) and a thumbwheel (154). Gear (144) is slidably and coaxially disposed on a proximal portion (150) of hub member (150) and is keyed to hub member (150), such that rotation of gear (144) will rotate hub member (150) and needle (110); yet hub member (150) and needle (110) may translate relative to gear (144). Gear (144) is rotatably driven by gear (744), as will be described in greater detail below. Alternatively, needle (110) may be rotated by rotating thumbwheel (154). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein. Examples of how needle (110) may be translated longitudinally relative to chassis (120) and top housing (130), particularly by a needle firing mechanism (400), will be described in greater detail below.

It should be understood that, as with other components described herein, needle (110) may be varied, modified, substituted, or supplemented in a variety of ways; and that needle (110) may have a variety of alternative features, components, configurations, and functionalities. A plurality of external openings (not shown) may also be formed in needle (110), and may be in fluid communication with second lumen (162). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Cutter (150) may also include one or more side openings (not shown). Of course, as with other components described herein, such external openings in needle (110) and cutter (150) are merely optional. As yet another merely illustrative example, needle (110) may be constructed in accordance with the teachings of U.S. Pub. No. 2008/0214955, the disclosure of which is incorporated by reference herein, and/or in accordance with the teachings of any other reference cited herein.

Probe (100) may also include a valve assembly in fluid communication with at least part of needle (110), selectively changing a pneumatic state of at least part of needle (110) based on any suitable conditions such as the longitudinal position of cutter (200). Such a valve assembly may be constructed in accordance with the teachings of U.S. Pub. No. 2010/0317997, the disclosure of which is incorporated by reference herein, in accordance with the teachings of U.S. Non-Provisional patent application Ser. No. 12/953,715, the disclosure of which is incorporated by reference herein, or otherwise. In addition or in the alternative, valving may be provided by vacuum source (800) and/or a vacuum canister, such as is taught in U.S. Pub. No. 2008/0214955, the disclosure of which is incorporated by reference herein. Other suitable alternative versions, features, components, configurations, and functionalities of needle (110) will be apparent to those of ordinary skill in the art in view of the teachings herein.

B. Exemplary Cutter Actuation Mechanism

As noted above, cutter (200) is operable to rotate and translate relative to needle (110) and past lateral aperture (114) to sever a tissue sample from tissue protruding through lateral aperture (114). This action of cutter (200) is provided by a cutter actuation mechanism (202). Cutter actuation mechanism (202) is positioned mainly in probe (100) in the present example, though it should be understood that cutter actuation mechanism (202) may be positioned mainly in holster (700) and/or do both in probe (100) and holster (700). Cutter actuation mechanism (202) includes meshing gears (140, 740), with gear (740) being driven by motor (204). Motor (204) is located in holster (700) in the present example, though it should be understood that motor (204) may alternatively be located in probe (100) and/or elsewhere.

By way of example only, cutter actuation mechanism (202) may be constructed in accordance with the teachings of U.S. Pub. No. 2008/0214955, the disclosure of which is incorporated by reference herein. As another merely illustrative example, cutter actuation mechanism (202) may be constructed in accordance with the teachings of U.S. Pub. No. 2010/0317997, the disclosure of which is incorporated by reference herein. As yet another merely illustrative example, cutter actuation mechanism (202) may be constructed in accordance with the teachings of U.S. Pub. No. 2010/0292607, entitled "Tetherless Biopsy Device with Self-Reversing Cutter Drive Mechanism," published Nov. 18, 2010, the disclosure of which is incorporated by reference herein. Alternatively, cutter actuation mechanism (202) may be constructed in accordance with the teachings of any other reference cited herein. It should also be understood that biopsy device (10) may be configured such that cutter (200) does not translate (e.g., such that cutter (200) merely rotates, etc.); or such that cutter (200) does not rotate (e.g., such that cutter (200) merely translates, etc.). As another merely illustrative example, cutter (200) may be actuated pneumatically in addition to or in lieu of being actuated by mechanical components. Other suitable alternative versions, features, components, configurations, and functionalities of cutter actuation mechanism (202) will be apparent to those of ordinary skill in the art in view of the teachings herein.

C. Exemplary Tissue Sample Holder

Tissue sample holder (300) of the present example comprises a plurality of chambers (not shown) configured to receive tissue samples that are severed by cutter (200) and communicated proximally through the hollow interior of cutter (200). Tissue sample holder (300) also includes one or more removable trays (not shown) that permit a user to remove severed tissue samples from tissue sample holder (300) without having to remove tissue sample holder (300) from chassis (120). Tissue sample holder (130) further includes a rotatable manifold (not shown) that is in fluid communication with vacuum source (800) and cutter (200) and that is rotatable to successively index the chambers to cutter (200). In particular, the manifold is rotated by a tissue sample holder rotation mechanism (302), which is driven by a motor (304). It should be understood that at least part of tissue sample holder rotation mechanism (302) and/or motor (304) may be incorporated into probe (100), into holster (700), or into both probe (100) and holster (700).

By way of example only, tissue sample holder (300) may be constructed and operable in accordance with the teachings of U.S. Pub. No. 2008/0214955, the disclosure of which is incorporated by reference herein. As another merely illustrative example, tissue sample holder (300) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. As yet another merely illustrative example, tissue sample holder (300) may be constructed an operable in accordance with the teachings of U.S. Pub. No. 2008/0221480, entitled "Biopsy Sample Storage," published Sep. 11, 2008, the disclosure of which is incorporated by reference herein.

In some other versions, tissue sample holder (300) does not include a rotatable manifold. In some such versions, tissue sample holder (300) is constructed in accordance with the teachings of U.S. Provisional Patent App. No. 61/381,466, entitled "Biopsy Device Tissue Sample Holder with Removable Basket," filed Sep. 10, 2010, the disclosure of which is incorporated by reference herein. Still other suitable ways in which tissue sample holder (300) may be constructed and operable will be apparent to those of ordinary skill in the art in view of the teachings herein.

III. Exemplary Holster

As shown in FIGS. 2-10, holster (700) of the present example includes a top housing cover (702), side panels (704), and a housing base (706), which are fixedly secured together. As best seen in FIG. 3 and as noted above, gears (740, 744) are exposed through top housing cover (702), and mesh with gears (140, 144) of probe (100) when probe (100) and holster (120) are coupled together. In particular, gears (740, 140) drive cutter actuation mechanism (202); while gears (744, 144) are employed to rotate needle (110). Holster (700) also includes a firing rod (730) and fork (732), which couple with needle (110) and fire needle (110) distally as will be described in greater detail below.

All motors (204, 304, 402) referred to herein are contained within holster (700) in the present example and receive power from an external source via cable (720). In addition or in the alternative, data may be communicated via cable (720) from holster (700) and/or to holster (700) as desired. In some other versions, motors (204, 304, 402) are powered by one or more batteries located within holster (700) and/or probe (100). It should therefore be understood that, as with other components described herein, cable (720) is merely optional. As yet another merely illustrative variation, motors (204, 304, 402) may be powered pneumatically, such that cable (720) may be substituted with a conduit communicating a pressurized fluid medium to holster (700). As still other merely illustrative variation, cable (720) may include one or more rotary drive cables that are driven by motors (204, 304, 402) that are located external to holster (700). It should also be understood that two or three of motors (204, 304, 402) may be combined as a single motor. Other suitable ways in which various mechanisms (202, 302, 400) may be driven will be apparent to those of ordinary skill in the art in view of the teachings herein.

A. Exemplary Needle Rotation Mechanism

As noted above, rotation of gear (744) provides rotation of needle (110) relative to probe (100). In the present example, gear (744) is rotated by rotating knob (710). In particular, knob (710) is coupled with gear (744) by a series of gears (not shown) and shafts (not shown), such that rotation of knob (710) rotates gear (744). A second knob (710) extends from the other side of holster (700). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (154). Various other suitable ways in which rotation of needle (110) may be provided will be apparent to those of ordinary skill in the art in view of the teachings herein. It should also be understood that some versions may provide no rotation of needle (110).

B. Exemplary Needle Firing Mechanism

Figure 4A:
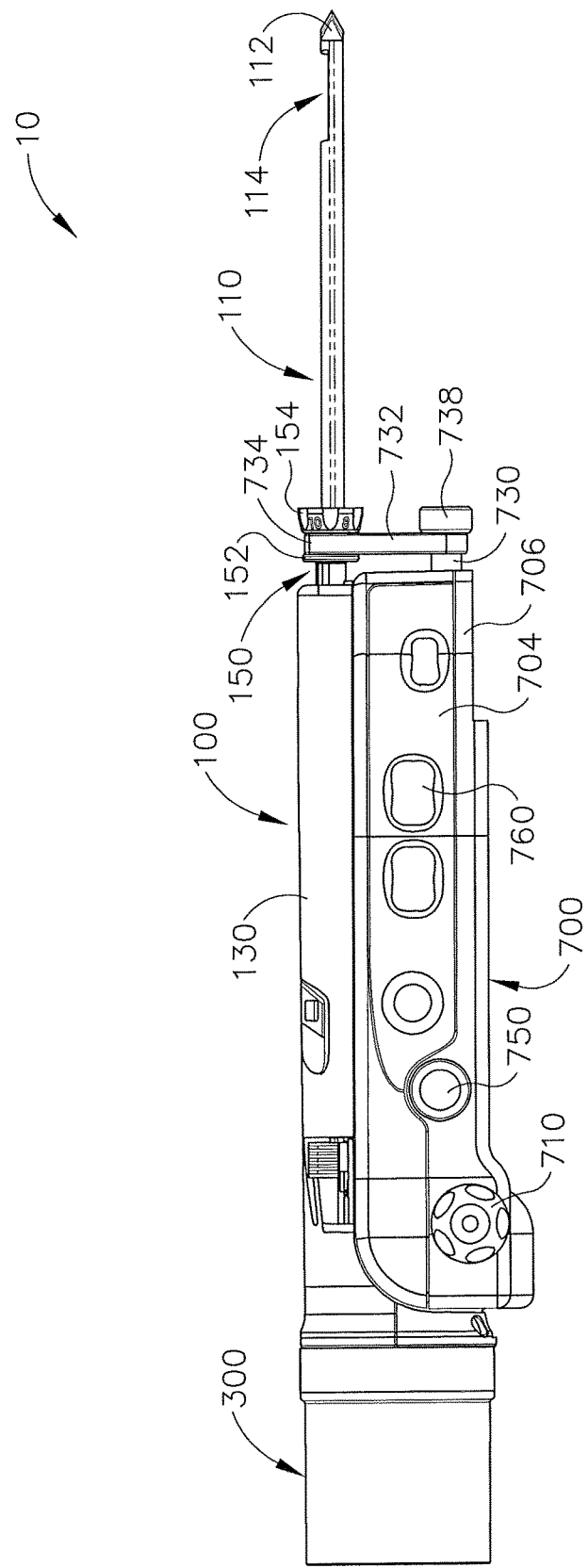
FIG. 4A depicts a side elevational view of the biopsy device of FIG. 2, with the needle in an armed position.
Figure 4B:
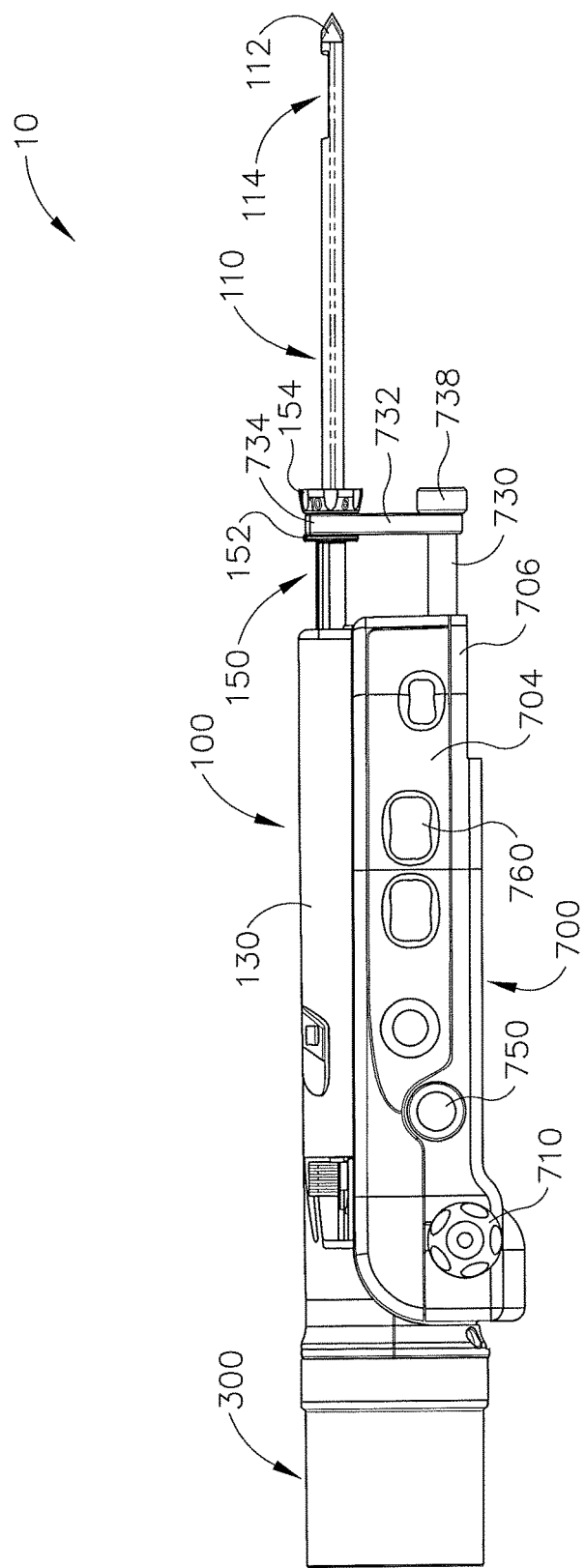
FIG. 4B depicts a side elevational view of the biopsy device of FIG. 2, with the needle in a fired position.

Holster (700) of the present example further includes a needle firing mechanism (400), which is operable to fire needle (110) from a loaded position as shown in FIG. 4A to a fired position as shown in FIG. 4B. By way of example only, such firing may be useful in instances where biopsy device (10) is mounted to a stereotactic table fixture or other fixture, with tip (112) adjacent to a patient's breast, such that needle firing mechanism (400) may be activated to drive needle (110) into the patient's breast. Needle firing mechanism (400) may be configured to drive needle (110) along any suitable range of motion, to drive tip (112) to any suitable distance relative to fixed components of probe (100). Needle firing mechanism (400) of the present example is activated by activation buttons (760) and arming buttons (750). Activation buttons (760) comprise thin film switches presented on side panels (704) of holster (700). In some versions activations buttons (760) are on both sides of holster (700) while in other versions activation buttons (760) are either on just one side of holster (700) or are located elsewhere (e.g., remote user interface, at vacuum source (800) or elsewhere, etc.). Activation buttons (760) are operable to selectively activate motor (402) as will be described in greater detail below. Arming buttons (750) are also provided on both sides of holster (700) in the present example, and are mechanically movable transversely relative to side panels (704). Each arming button (750) includes a bellows (752) that provides a fluid tight seal with side panel (704). Of course, either type of button (750, 760) may have various other components, features, configurations, and operabilities.

In the present example, needle firing mechanism (400) is coupled with needle (110) via a firing rod (732) and a firing fork (732). Firing rod (732) and firing fork (734) are unitarily secured together by complementary flats (736, 737) and a pin (738). Firing fork (732) includes a pair of prongs (734) that receive hub member (150) of needle (110) therebetween. Prongs (734) are positioned between annular flange (152) and thumbwheel (154), such that needle (110) will translate unitarily with firing rod (730) and fork (732). Prongs (734) nevertheless removably receive hub member (150), such that fork (732) may be readily secured to hub member (150) when probe (100) is coupled with holster (700); and such that hub member (150) may be readily removed from fork (732) when probe (100) is decoupled from holster (700). Prongs (734) are also configured to permit hub member (150) to rotate between prongs (734), such as when knob (710) is rotated to change the angular orientation of lateral aperture (114). Other suitable components, configurations, and relationships will be apparent to those of ordinary skill in the art in view of the teachings herein.

Figure 6:
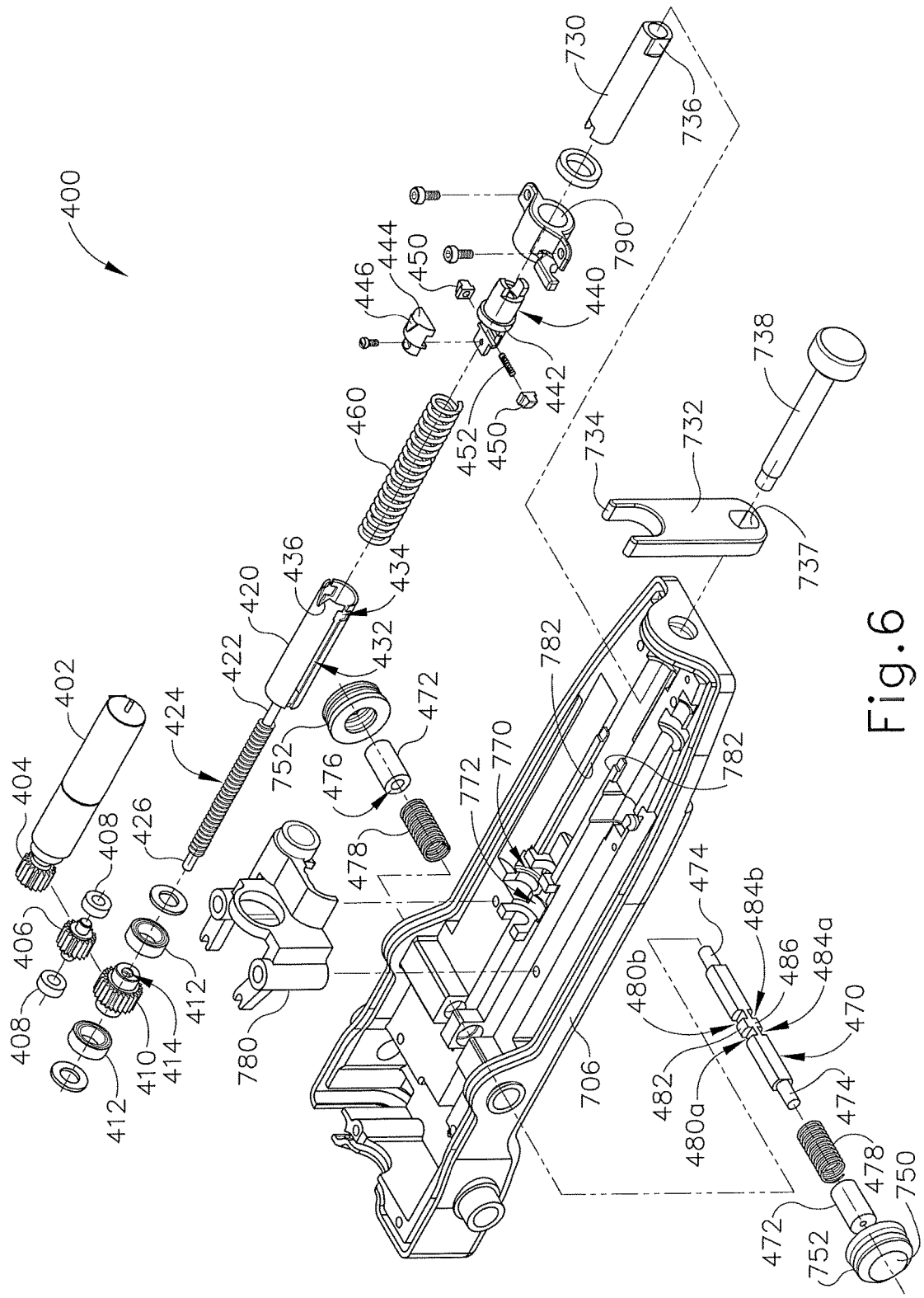
FIG. 6 depicts an exploded perspective view of the needle firing mechanism of the holster of FIG. 5.

FIGS. 5-10 show components of needle firing mechanism (400) in greater detail. As best seen in FIG. 6, needle firing mechanism (400) of this example includes motor (402), a firing tube (420), a coupling (440), and a coil spring (460). As will be described in greater detail below, motor (402) is operable to selectively couple firing tube (420) with coupling (440), thereby compressing coil spring (460). Motor (402) is further operable to retract needle (110) to the loaded position shown in FIG. 4A. Motor (402) is then operable to decouple coupling (440) from firing tube (420), allowing coil spring (460) to fire needle (110) distally to the fired position shown in FIG. 4B. Of course, a variety of other types of resilient or biasing components may be used in addition to or in lieu of coil spring (460).

Still referring to FIG. 6, motor (402) includes an integral drive gear (404), such that motor (402) rotates drive gear (404) when activated. Drive gear (404) meshes with intermediate gear (406), which is supported in recess (770) of housing base (706) by bushings (408). Intermediate gear (406) meshes with nut gear (410), which is supported in recess (772) of housing base (706) by bushings (412). Nut gear (410) includes internal threading (414) and is coaxially disposed about a shaft (422) that extends proximally and unitarily from firing tube (420). In particular, shaft (422) includes external threading (424) that complements internal threading (414) of nut gear (410). As will be described in greater detail below, shaft (422) does not rotate relative to housing base (706) in this example. It should therefore be understood that rotation of nut gear (410) causes firing tube (420) to translate longitudinally. In other words, motor (402) may be activated to translate firing tube (420) distally or proximally, depending on the direction in which motor (402) rotates drive gear (404). A retainer (780) is secured to housing base (706) to retain motor (402), gears (404, 406, 410), and bushings (408, 412) relative to housing base (706).

Figure 7:
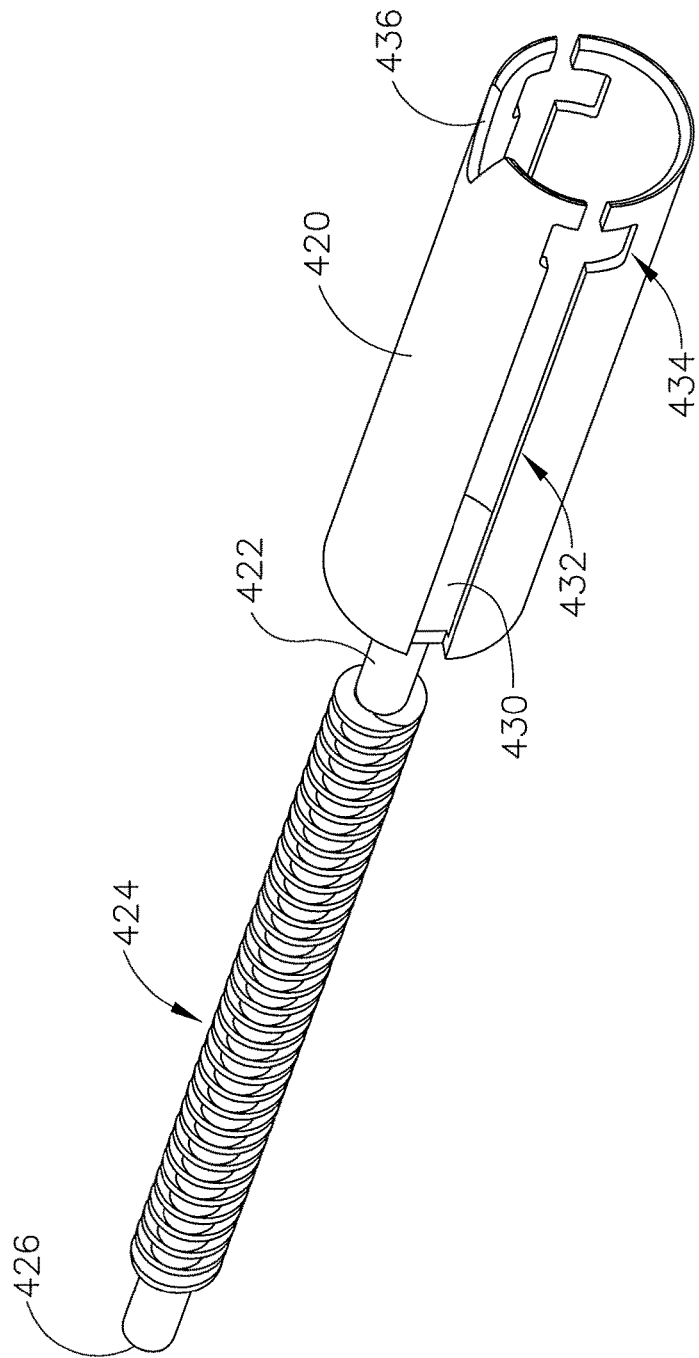
FIG. 7 depicts a side view of the lead screw and the firing tube of the needle firing mechanism of FIG. 6.

As best seen in FIG. 7, firing tube (420) further includes a proximal interior wall (430), a pair of opposing elongate slots (432), a pair of pawl notches (434) associated with slots (432), and an alignment notch (436). As best seen in FIG. 8, housing base (706) includes a pair of opposing inwardly projecting cam rails (782) that are disposed in elongate slots (432) of firing tube (420). Rails (782) permit firing tube (420) to translate relative to housing base (706) but prevent firing tube (420) from rotating relative to housing base (706). Of course, a variety of other types of structures, components, features, etc. may be used to provide such operability, if desired.

Coupling (440) is secured to firing rod (730) and pin (738), such that coupling (440) translates unitarily with rod (730), pin (738), fork (732), and needle (110). Coupling (440) includes an annular flange (442) and a cap member (444). Cap member (444) includes an alignment protrusion (446) that complements alignment notch (436) of firing tube (420). Coupling (440) also includes a pair of pawls (450) that are resiliently biased to project opposingly outwardly by a spring (452). Of course, a variety of other types of resilient or biasing components may be used in addition to or in lieu of coil spring (452). Cap member (444) secures pawls (450) and spring (452) to coupling while allowing pawls (450) to move transversely as spring (452) is compressed and decompressed. In particular, and as will be described in greater detail below, pawls (450) are sized, positioned, and configured to snap into pawl notches (434) of firing tube (420) as firing tube (420) is advanced distally; then to be deflected inwardly by rails (782) as firing tube (420) is retracted proximally.

Referring back to FIG. 6, needle firing mechanism (400) of the present example further includes a transverse bar (470) that is positioned between buttons (750) and that is movable transversely relative to housing base (706). A pair of spacers (472) are positioned between the free ends of transverse bar (470) and buttons (750). Each free end of transverse bar (470) includes a post (474) that is received in a corresponding recess (476) of spacer (472). A pair of coil springs (478) are positioned coaxially about transverse bar (470). Each coil spring (478) resiliently bears against a corresponding spacer (472) and housing base (706). Coil springs (478) are thus configured to bias transverse bar (470) to a transversely centered position relative to housing base (706). Of course, a variety of other types of resilient or biasing components may be used in addition to or in lieu of coil springs (478). As also shown in FIG. 6, transverse bar (470) includes a pair of upper recesses (480a, 480b) and a pair of lower recesses (484a, 484b). Upper recesses (480a, 480b) are separated by an upper protrusion (482); while lower recesses (484a, 484b) are separated by a lower protrusion (486). As shown in FIGS. 5, 9A-9B, and 9D, transverse bar (470) is configured such that protrusions (482, 486) are centered on a vertical plane (coming out of the page) that is aligned with the longitudinal axis of shaft (422), firing tube (420), coupling (440), firing rod (730), and pin (738) when transverse bar (470) is centered by opposing resilient biases of coil springs (478).

In an exemplary operation of needle firing mechanism (400), components of needle firing mechanism (400) are initially in the positions shown in FIG. 5. The user then activates one of buttons (760) to arm needle firing mechanism (400). This causes motor (402) to rotate drive gear (404) in a first direction, which through intermediate gear (406) causes nut gear (410) to rotate in the same first direction. This rotation of nut gear (410) advances firing tube (420) distally, due to interaction between internal threads (414) of nut gear (410) and external threads (424) of shaft (422). Firing tube (420) eventually reaches the position shown in FIG. 9A. As firing tube (420) advances from the position shown in FIG. 5 to the position shown in FIG. 9A, coil spring (460) is compressed between proximal interior wall (430) of firing tube (420) and coupling (440). In addition, as firing tube (420) advances from the position shown in FIG. 5 to the position shown in FIG. 9A, pawls (450) are deflected inwardly by the distal end of firing tube (420) and then snap outwardly into pawl notches (434) of firing tube (420) once firing tube (420) reaches the position shown in FIG. 9A. This inward deflection and outward snapping is facilitated by coil spring (452), which provides an outward bias to pawls (450) while still allowing pawls (450) to be moved inwardly toward each other. It should also be understood that, as firing tube (420) advances from the position shown in FIG. 5 to the position shown in FIG. 9A, interaction between alignment notch (436) and alignment protrusion (446) ensures that firing tube (420) and coupling (440) are properly rotationally aligned, thereby ensuring that pawls (450) reach pawl notches (434) when firing tube (420) reaches the distal-most position shown in FIG. 9A.

Figure 9A:
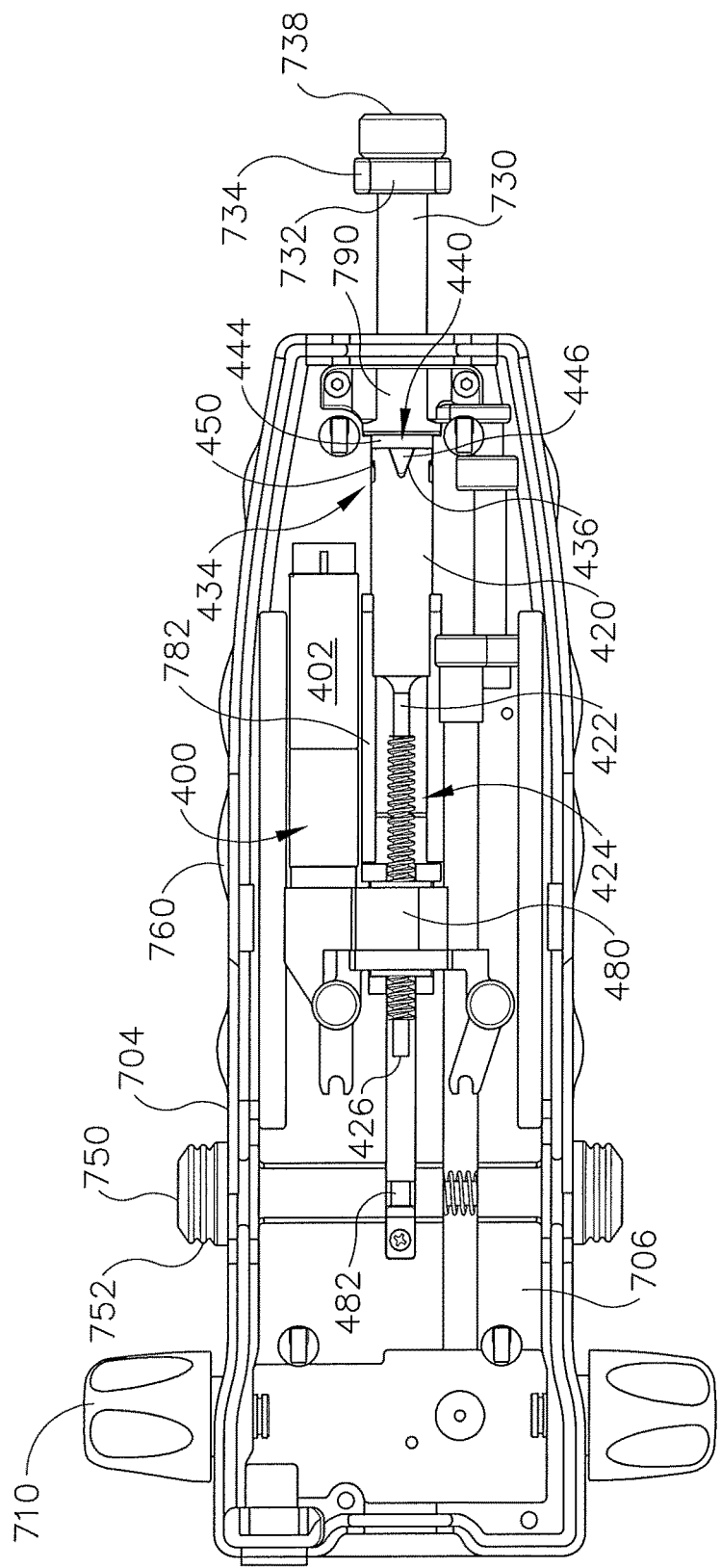
FIG. 9A depicts a top plan view of the holster of FIG. 5, with the needle firing mechanism in a pre-armed configuration.

After having reached the configuration shown in FIG. 9A, where firing tube (420) has engaged coupling (440), the operation of motor (402) is reversed such that drive gear (404) and nut gear (410) are rotated in a second direction that is opposite to the first direction. In some versions, this requires a separate activation of at least one button (760). In some other versions, a single activation of button (760) causes motor (402) to drive firing tube (420) to the position in FIG. 9A and automatically reverse as soon as it reaches that position. As another merely illustrative example, a user must hold down at least one button (760) the entire time to activate motor (402) to drive firing tube (420) to the position in FIG. 9A and automatically reverse as soon as it reaches that position. In versions where motor (402) automatically reverses as soon as firing tube (420) reaches the position shown in FIG. 9A, there are various ways in which such automatic reversal may be provided. By way of example only, an encoder, proximity sensor, motor load detection algorithm, and/or various other components/techniques may be used to provide automatic reversal of motor (402). It should also be understood that a sensor may be used to detect latching of pawls (450) to firing tube (420), and this data may be used to trigger reversal of motor (402). As yet another merely illustrative example, biopsy device (10) may provide an alert to a user (e.g., a beep, a light, a loud click when pawls (450) snap into engagement with firing tube (420), etc.) when firing tube (420) reaches the position shown in FIG. 9A, such that the user must then provide an input (e.g., through one or more buttons (750, 760) and possibly an additional mechanical safety, etc.) to cause motor (402) to reverse in order to continue the firing process.

With nut gear (410) being rotated in the second direction, firing tube (420) is retracted proximally, due to interaction between internal threads (414) of nut gear (410) and external threads (424) of shaft (422). Firing tube (420) eventually reaches the armed position shown in FIG. 9B. In this configuration, coil spring (460) remains compressed between proximal interior wall (430) of firing tube (420) and coupling (440), storing significant potential energy that is resisted by engagement of pawls (450) with firing tube (420). Pawls (450) are just distal to rails (782) and are still engaged with firing tube (420) in the configuration shown in FIG. 9B. In addition, transverse bar (470) is positioned and configured to restrict further proximal movement of firing tube (420). In particular, with transverse bar (470) being centered by springs (478), lower protrusion (486) is positioned just proximal to the proximal end (426) of shaft (422); and along a longitudinal axis passing through shaft (422). While only upper protrusion (482) can be seen in FIG. 9B, it should be understood that lower protrusion (486) is just beneath upper protrusion (482). Of course, in some other versions upper protrusion (482) may be positioned just proximal to the proximal end (426) of shaft (422); and along a longitudinal axis passing through shaft (422). In the event that motor (402) is inadvertently activated to continue translating firing tube (420) proximally, the proximal end (426) of shaft (422) will almost immediately run into lower protrusion (486), which will prevent further proximal movement of firing tube (420). In other words, firing tube (420) cannot move further proximally until lower protrusion (486) is moved out of the way as described in further detail below. It should also be understood that these components are configured such that pawls (450) remain engaged with firing tube (420) until lower protrusion (486) is moved out of the way as described in further detail below.

Figure 9B:
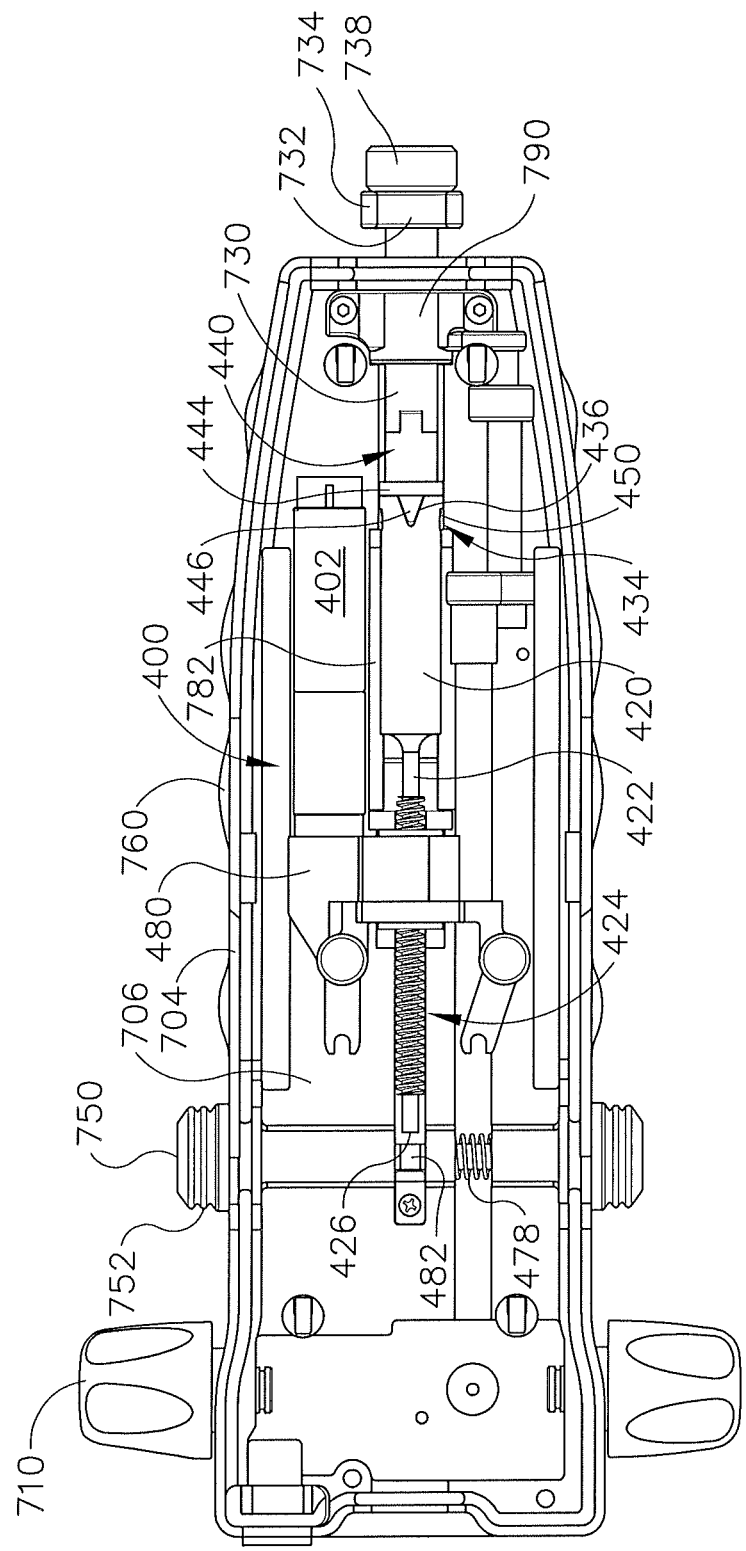
FIG. 9B depicts a top plan view of the holster of FIG. 5, with the needle firing mechanism in an armed configuration.
Figure 9C:
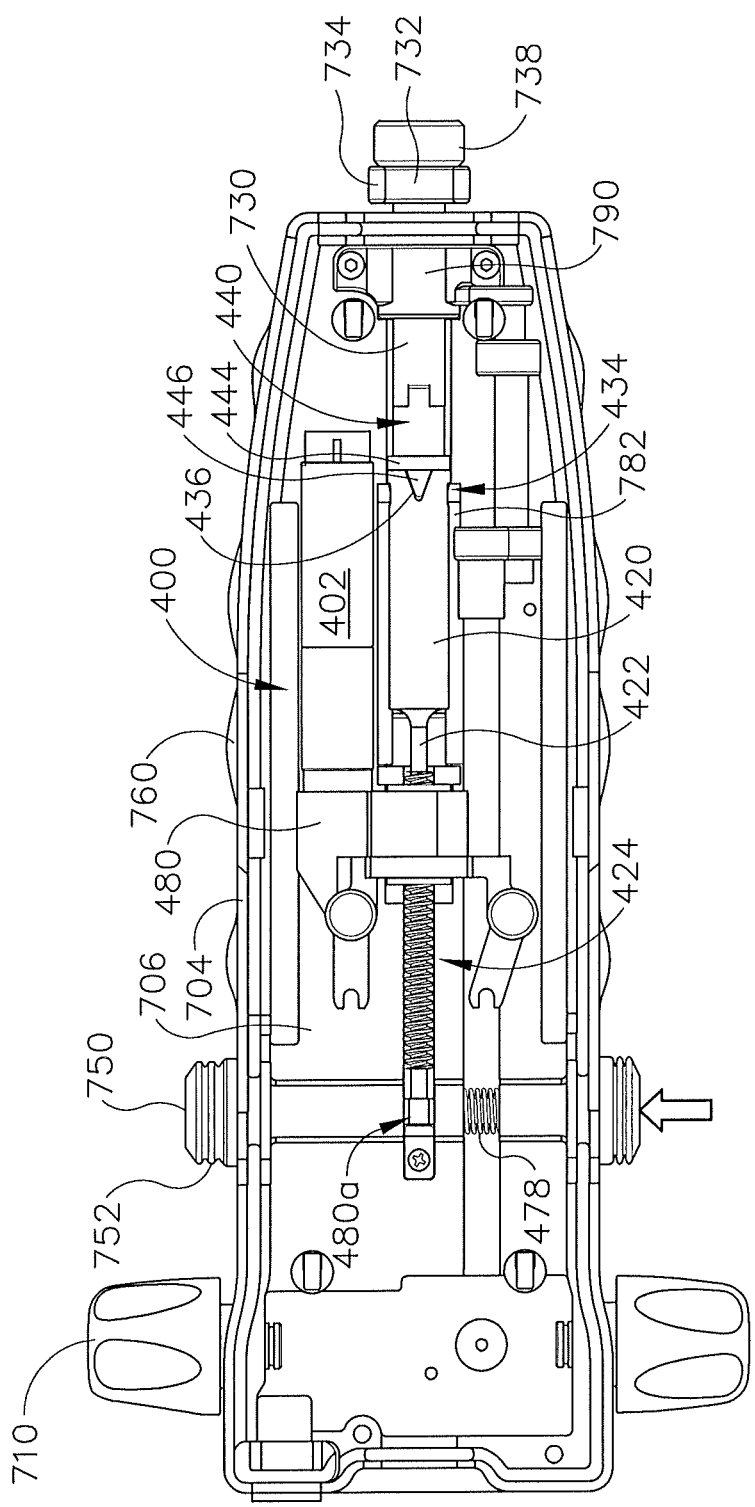
FIG. 9C depicts a top plan view of the holster of FIG. 5, with the needle firing mechanism in a firing configuration.
Figure 9D:
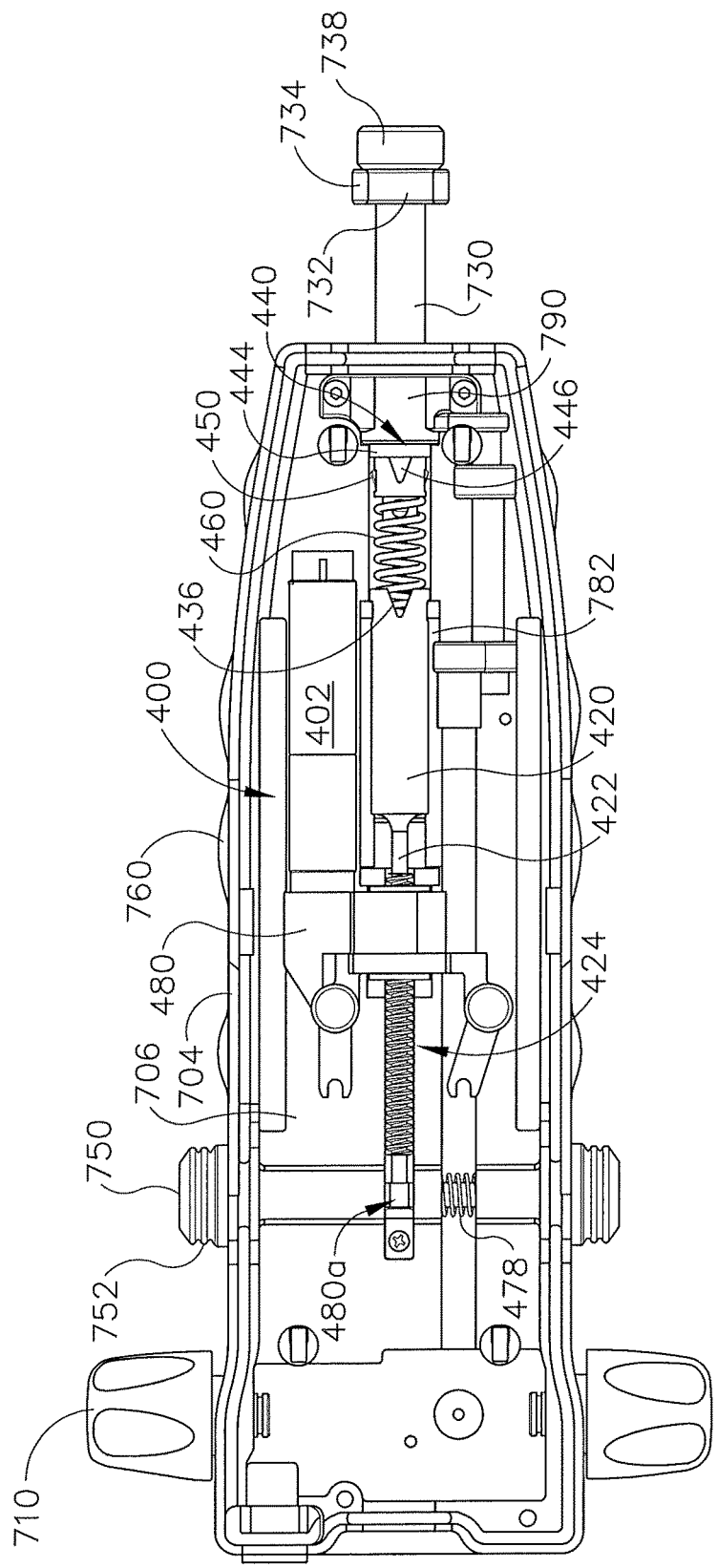
FIG. 9D depicts a top plan view of the holster of FIG. 5, with the needle firing mechanism in a fired configuration.
Figure 10:
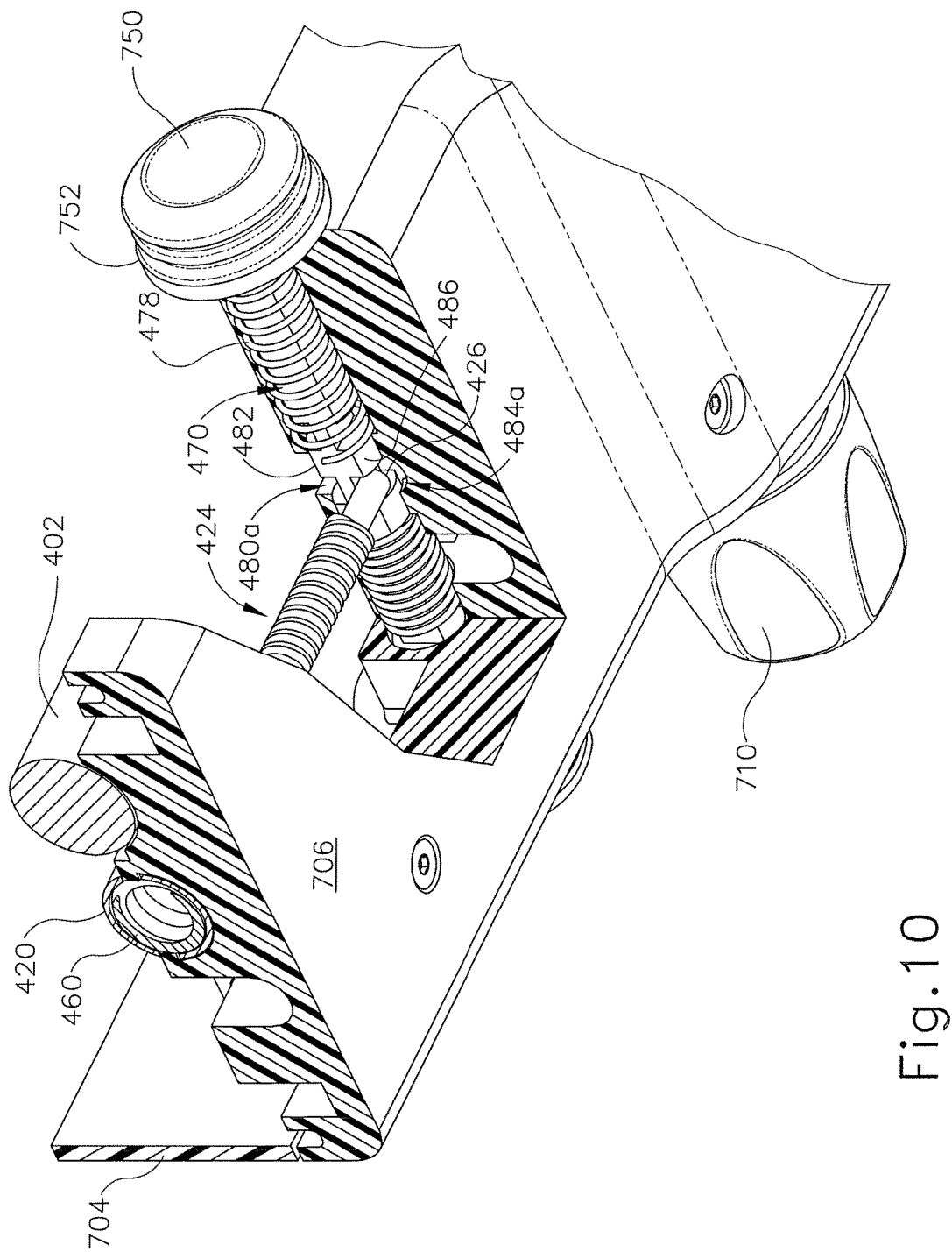
FIG. 10 depicts a partial perspective view of components of the needle firing mechanism of FIG. 6, with the needle firing mechanism in the firing configuration of FIG. 9C.

After needle firing mechanism (400) has reached the armed configuration shown in FIG. 9B, needle firing mechanism (400) is ready to be fired. Biopsy device (10) may include one or more user feedback features (e.g., one or more lights, one or more speakers or other sound emitting components, etc.) to alert the user that needle firing mechanism (400) has reached the armed configuration. In order to fire needle firing mechanism (400), the user must hold in one of buttons (750) while activating another button (760). This will allow firing of needle firing mechanism (400) as shown in FIG. 9C. While the button (750) on the right-hand side of holster (700) is shown as depressed in FIG. 9C, it should be understood that the same operation may be provided by depressing the button (750) on the left-hand side of holster (700). This pressing of button (750) pushes transverse bar (470) such that transverse bar (470) moves laterally relative to holster (700). This lateral movement of transverse bar (470) moves lower protrusion (486) out of the way relative to the proximal end (426) of shaft (422). This can be better seen in FIG. 10, which shows lower recess (484a) providing clearance for further proximal movement of proximal end (426) of shaft (422). With such clearance being provided, motor (402) is activated to translate firing tube (420) further proximally to the positions shown in FIGS. 9C and 10. With firing tube (420) in this position, pawls (450) are brought into contact with rails (782), which push pawls (450) inwardly toward each other. In particular, rails (782) push pawls (450) inwardly far enough such that pawls (450) disengage pawl notches (434). With pawls (450) disengaged from pawl notches (434), coupling (440) is disengaged from firing tube (420). With coupling (440) disengaged from firing tube (420), there is nothing to prevent coil spring (460) from decompressing. Coil spring (460) thus immediately and forcefully decompresses, rapidly pushing coupling (440) distally to fire needle (110) via firing bar (730) and fork (732) as shown in FIG. 9D. Annular flange (442) and retainer (790) cooperate to arrest distal movement of coupling (440) once coupling (440) reaches the fired position shown in FIG. 9D.

In some versions, biopsy device permits the user to "soft fire" needle (110). For instance, in some such versions, motor (402) is activated to move distally to translate firing tube (420) distally to the position shown in FIG. 9A, to engage pawls (450). Motor (402) is then reversed to translate firing tube (420), fork (732), needle (110), and associated components proximally to the position shown in FIG. 9B. However, instead of continuing to rotate in that direction to continue translating firing tube (420) further proximally, to release pawls (450) and allow coil spring (460) to fire fork (732) and needle (110) distally, motor (402) again reverses to advance these components distally back to the configuration shown in FIG. 9A. In other words, motor (402) is used to drive fork (732) and needle (110) instead of using coil spring (460) to drive fork (732) and needle (110) distally. It should be understood that such operation may allow the distal translation speed of fork (732) and needle (110) to be controlled selectively, and may also allow the distal motion of fork (732) and needle (110) to be interrupted, slowed or sped up, or otherwise controlled as fork (732) and needle (110) traverse a distal range of motion. Of course, such "soft fire" control may be provided through one or more buttons (750, 760) and/or through any other suitable form of control. It should be understood that, in some versions, a "soft fire" firing of needle (110) may be less audible to the patient than firing of needle (110) by coil spring (460).

With needle (110) having been fired as shown in FIG. 9D (or as shown in FIG. 9A in "soft fire" operations, etc.), the user may then activate cutter actuation mechanism (202) to acquire one or more biopsy samples from the patient's breast. In some versions, right after needle firing mechanism (400) has fired needle (110) distally, motor (402) automatically again reverses direction to move components from the configuration shown in FIG. 9D back to the configuration shown in FIG. 9A, thus getting ready for a subsequent firing stroke. Alternatively, needle firing mechanism (400) may wait for a user to press arming button (760) before motor (402) reverses direction to move components from the configuration shown in FIG. 9D back to the configuration shown in FIG. 9A. Other suitable ways in which biopsy device (10) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy device, comprising:
   (a) a needle having a tissue piercing tip and an opening;
   (b) a body portion, wherein the needle is longitudinally movable relative to the body portion; and
   (c) a needle firing assembly, wherein the needle firing assembly includes:
      (i) a resilient member configured to urge the needle distally relative to the body portion when the resilient member is in a loaded configuration,
      (ii) a first translating member, and
      (iii) a second translating member, wherein the second translating member is secured relative to the needle such that the second translating member and the needle translate unitarily relative to the body portion, wherein the first translating member is movable distally toward the second translating member to load the resilient member,
      wherein the first and second translating members are removably securable to each other to hold the resilient member in the loaded configuration,
      wherein the first and second translating members are movable proximally together while secured to each other,
      wherein the second translating member is configured to release from the first translating member when the first and second translating members together reach a proximal position, wherein the loaded resilient member is configured to drive the second translating member distally relative to the first translating member upon release of the second translating member from the first translating member.

2. The biopsy device of claim 1, wherein the needle firing assembly includes a motor, wherein the motor is operable to selectively drive the first translating member in the distal direction and in the proximal direction.

3. The biopsy device of claim 2, wherein the first translating member and the second translating member are operable to cooperatively drive the resilient member into a compressed position as the first translating member is driven in the distal direction by the motor.

4. The biopsy device of claim 3, wherein the first and second translating members are configured to maintain the resilient member in the compressed position as the first and second translating members are moved proximally together while secured to each other.

5. The biopsy device of claim 4, wherein the body portion includes a feature configured to release the second translating member from the first translating member when the first and second translating members reach a proximal position, wherein the release of the second translating member from the first translating member allows the resilient member to decompress to fire the needle distally.

6. The biopsy device of claim 5, wherein the feature configured to release the second translating member from the first translating member includes a cam rail, wherein the first translating member includes an elongate slot, wherein the cam rail is disposed in the elongate slot.

7. The biopsy device of claim 1, wherein the resilient member includes a coil spring.

8. The biopsy device of claim 1, wherein the needle firing assembly further includes a firing rod and a fork, wherein the fork is removably secured to the needle, wherein the fork is secured to the firing rod, wherein the firing rod is secured to the second translating member such that the firing rod and fork are translatable relative to the body portion.

9. The biopsy device of claim 8, wherein the resilient member is coaxial with the firing rod, wherein the resilient member and the firing rod are parallel to the needle, wherein the resilient member and the firing rod are laterally offset from the needle.

10. The biopsy device of claim 9, wherein the second translating member includes at least one resiliently biased pawl configured to selectively secure the second translating member to the first translating member.

11. The biopsy device of claim 1, wherein the needle firing assembly further includes a movable restriction member configured to restrict proximal movement of the first translating member to selectively prevent firing of the needle firing assembly.

12. The biopsy device of claim 11, wherein the restriction member includes a transverse bar, wherein the transverse bar includes an obstruction feature and a clearance feature, wherein the obstruction feature is configured to arrest proximal movement of the first translating member when the transverse bar is in a first position and when the first translating member reaches a first proximal position, wherein the clearance feature is configured to provide clearance for the first translating member to move to a second longitudinal position when the transverse bar is in a second position, wherein the second longitudinal position is proximal to the first longitudinal position.

13. The biopsy device of claim 12, wherein the restriction member further includes at least one resilient member configured to bias the transverse bar to the first position.

14. The biopsy device of claim 1, wherein the first translating member includes a firing tube.

15. The biopsy device of claim 14, wherein at least a portion of the resilient member is disposed within the firing tube.

16. A biopsy device, comprising:
(a) a needle having a tissue piercing tip and an opening;
(b) a body portion, wherein the needle is longitudinally movable relative to the body portion; and
(c) a needle firing assembly, wherein the needle firing assembly includes:
(i) a resilient member configured to urge the needle distally relative to the body portion,
(ii) a translating member, wherein the translating member is operable to compress the resilient member when the translating member is moved distally, and
(iii) a coupling assembly, wherein the coupling assembly is selectively attachable to the translating member to hold the resilient member in a compressed configuration.

17. The biopsy device of claim 16, wherein the needle firing assembly further includes a motor, wherein the motor is operable to drive the translating member distally relative to the body portion to secure the translating member and the coupling assembly thereby placing the resilient member in the compressed configuration.

18. The biopsy device of claim 17, wherein the motor is further operable to drive the translating member proximally to a first proximal position while the translating member and coupling assembly are attached to each other, wherein the motor is further operable to drive the translating member proximally to a second proximal position to detach the translating member and the coupling assembly, to thereby fire the needle distally.

19. The biopsy device of claim 16, wherein the translating member includes a threaded region, wherein the needle firing assembly further includes a nut rotatably coupled with the motor, wherein the nut has threading complementing the threaded region of the translating member.

20. A method of operating a biopsy device, wherein the biopsy device comprises a needle, a body portion, a first translating member, a second translating member, and a resilient member, wherein the needle, the first translating member, and the second translating member are translatable relative to the body portion, wherein the second translating member is secured relative to the needle such that the needle and the second translating member translate unitarily, the method comprising:
(a) advancing the first translating member distally relative to the body portion to load the resilient member;
(b) coupling the first translating member with the second translating member;
(c) retracting the first and second translating members proximally relative to the body portion to a proximal position, wherein the resilient member remains loaded during the act of retracting; and
(d) releasing the second translating member from the first translating member when the first and second translating members reach the proximal position, thereby firing the second translating member distally relative to the body portion under the influence of the loaded resilient member.

* * * * *